United States Patent [19]

Cone

[11] 4,394,321
[45] Jul. 19, 1983

[54] TRIARYLBORANEISOCY ANO METAL COMPOUNDS

[75] Inventor: Michael M. Cone, Orange, Tex.

[73] Assignee: E. I. Du Pont de Nemours and Company, Wilmington, Del.

[21] Appl. No.: 320,216

[22] Filed: Nov. 12, 1981

[51] Int. Cl.$^3$ .................... C07F 15/04; C07F 5/02
[52] U.S. Cl. .................... 260/439 R; 260/429 R; 260/430; 260/431; 260/438.1; 260/429.9; 260/465.8 R; 568/1
[58] Field of Search ............ 260/438.1, 439 R, 429 R, 260/465.8 R, 430, 431, 429.9; 568/1

[56] References Cited

U.S. PATENT DOCUMENTS

| | | | |
|---|---|---|---|
| 3,644,453 | 2/1972 | Onsager | 260/438.1 |
| 3,644,455 | 2/1972 | Onsager | 260/439 R |
| 3,676,481 | 7/1972 | Chia | 260/439 R X |
| 3,766,231 | 10/1973 | Gosser et al. | 260/439 R |
| 3,773,809 | 11/1973 | Walter | 260/465.8 R |
| 3,846,461 | 11/1974 | Shook | 260/439 R |
| 3,847,959 | 11/1974 | Shook et al. | 260/439 R |
| 3,859,092 | 1/1975 | Gysling et al. | 260/438.1 X |
| 3,860,500 | 1/1975 | Gysling | 260/438.1 |
| 3,868,398 | 2/1975 | Kroll et al. | 260/438.1 |
| 3,927,055 | 12/1975 | Gysling | 260/438.1 |
| 3,980,654 | 7/1976 | Gysling | 260/438.1 X |
| 3,989,732 | 11/1976 | Gysling | 260/438.1 |
| 4,082,811 | 4/1978 | Shook | 568/1 |
| 4,134,923 | 1/1979 | Reimer | 568/1 |

FOREIGN PATENT DOCUMENTS 2047680 12/1980 United Kingdom .

Primary Examiner—Helen M. S. Sneed

[57] ABSTRACT

Bis(triarylboraneisocyano-N)-tetrakis-(alkylnitrile) and bis(triarylboraneisocyano-N)-bis-(alkyldinitrile) metal compounds.

10 Claims, No Drawings

TRIARYLBORANEISOCYANO METAL COMPOUNDS

BACKGROUND OF THE INVENTION

1. Field of the Invention

The present invention relates to novel boron containing metal compounds and methods for the preparation thereof, and more particularly to bis(triarylboraneisocyano-N)-tetrakis(alkylnitrile) and bis(triarylboraneisocyano-N)-bis(alkyldinitrile) metal compounds, e.g., bis(triphenylboraneisocyano-N)-bis-(adiponitrile)nickel(II).

2. Description of the Prior Art

Numerous boron containing cyanide complexes have been described. A compound postulated to be the sodium cyanide adduct of triphenylborane having the formula [$\phi_3$(NC)B]Na was reported by G. Wittig et al [*Ann. Chem.* 573, 195 (1951)]. The synthesis of Rn($\eta$-$C_5H_5$) $(CO)_2NCBO_3$ and its thermal rearrangement to Ru($\eta$-$C_5H_5$) $(CO)_2Cn$ and Ru($\eta$-$C_5H_5$) $(CO)_2CNBO_3$ are reported by R. J. Haines et al, *Journal of Organometallic Chemistry*, 84, 357 (1975). A compound having Fe-C-N-$BO_3$ bonding is reported by M. Laing et al *Journal of Organometallic Chemistry*, 82, C 40-42 (1974).

U.S. Pat. No. 4,082,811 issued on Apr. 4, 1978 discloses complexes containing triarylborane and nickel cyanide (oxidized zero-valent nickel), but the patentee does teach that the relative amounts of nickel and boron can vary from minor amounts of triphenylborane to about two moles of the borane per mole of nickel. This implies a mixture of materials. The patentee further discloses that the amine adduct of triphenylborane e.g., the ammonia adduct, is formed when the solids are contacted with a nitrogen-containing base.

British Pat. No. 2,047,680 issued on Dec. 3, 1980 discloses compounds having the general formula $Ni[NH_3]_4[(NC)B(C_6H_4-R)_3]_2$ wherein R is hydrogen, halogen, alkyl and aryl groups and which were prepared, for example, by reacting the alkali metal cyanide adduct of triphenylborane with a nickel halide, e.g., $NiCl_2$.

A general discussion of nitrile functions and their ability to bond to metals is found in "Advanced Inorganic Chemistry", F. A. Cotton and G. Wilkinson, 4 Ed. p. 142 John Wiley & Sons (1980). In an article by D. L. Greene et al, *Journal of Inorganic and Nuclear Chemistry*, 35, 1471 (1973) there is a discussion of the spectral consequences of forming different kinds of complexes with dinitriles.

SUMMARY OF THE INVENTION

This invention is directed to novel compounds having the general formula:

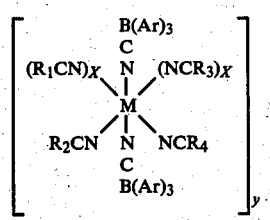

wherein X is 0 or 1, Y is a positive integer of 1-50, M is a metal selected from the class of metals of groups IIA, IB, IIB, VIIB and VIII; provided that when M is Pd, Ag, Cd, Pt, Au or Hg, X is 0; Ar is an aryl or substituted aryl group having 6-10 carbon atoms; $R_1$, $R_2$, $R_3$ and $R_4$ are the same or different and are groups selected from the class consisting of alkyl and substituted alkyl groups having 1-6 carbon atoms, alkenyl and substituted alkenyl groups having 2-6 carbon atoms, and aryl groups having 6-10 carbon atoms and also wherein the $R_1$-$R_4$ groups which are attached to adjacent nitrile groups can be intermolecularly or intramolecularly cojoined and are selected from the class consisting of alkylene groups having 1-4 carbon atoms.

Of particular interest are compounds of the general formula:

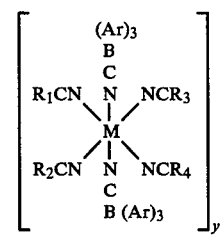

wherein y is a positive integer of 1-50; M is a metal ion selected from the class consisting of $Ni^{++}$, $Fe^{++}$ and $Fe^{+++}$; Ar is selected from the group consisting of phenyl, orthotolyl, paratolyl and mixtures thereof; $R_1$-$R_4$ are the same or different and are groups selected from the class consisting of 1-methyl-1-propenyl, 1-methyl-2-propenyl, 1-butenyl, 2-butenyl, 3-butenyl and butyl or wherein the $R_1$-$R_4$ groups are attached to adjacent nitrile groups and are cojoined intermolecularly or intramolecularly and are groups selected from the class consisting of ethylidene and ethylene.

These compounds contain boron combined with organocyano compounds in a relatively stable molecule which permits ready separation of the compound from other organics and purification of the compounds. If desired, the compounds may be reacted to recover the boron, nitrile and metal values.

DETAILED DESCRIPTION OF THE INVENTION

The compounds of the present invention can be monomeric, oligomeric or polymeric, if the neutral ligands are dinitriles. In compounds with dinitrile ligands these ligands may have a free, unbound group; or they may be bridging, that is intermolecularly cojoined; or they may be chelating, that is intramolecularly cojoined. Generally, the number of monomer units in a polymeric compound will not exceed 50. The higher molecular weight compounds, e.g., y=20 or greater, tend to be solid while the compounds in solution tend to exhibit a lower molecular weight, e.g., y=5 or less.

The monomeric compounds made from mononitriles, and the bridged or chelated structures made from dinitriles show two nitrile absorption bands in their infrared spectra; one for the cyanoborate, and one for the alkylnitrile moiety. Each of these infrared resonances is shifted approximately 20-50 $cm^{-1}$ towards shorter wavelengths from its uncoordinated position. Nonchelated monomeric compounds made from dinitriles show three alkylnitrile absorptions; the third being the uncoordinated part of the dinitrile. It also has been determined that all nickel is bonded only to nitrogen, and that all nickel-nitrogen bond lengths are identical.

The metals, corresponding to "M" in the above formula, with which the nitrile and boron moieties are coordinated are the metals as set forth in the Periodic Table of the Elements as Group IIA—particularly Mg and Ca; Group IB—particularly Cu and Ag; Group IIB—particularly Zn and Cd; Group VIIB—particularly Mn; Group VIII—particularly Fe, Co, Ni, Ru, Rh and Pd. These metals are most conveniently introduced into the reaction medium as their salts of inorganic Bronsted acids, e.g., sulfate, chloride and nitrate or the hydrates of these salts. Specific examples include nickel chloride, nickel chloride hexahydrate, magnesium chloride hexahydrate, calcium chloride, copper (II) chloride dihydrate, silver nitrate, zinc (II) nitrate, cadmium chloride hydrate, manganese (II) nitrate hexahydrate, ferrous sulfate heptahydrate, ferric chloride, cobaltous chloride hexahydrate, ruthenium (III) chloride and rhodium (III) chloride.

The cyanide can be introduced as hydrogen cyanide or as an alkali metal cyanide, e.g., sodium potassium or lithium cyanide.

The trisubstituted boranes (corresponding to $B(Ar_3)$ in the above formula) can be introduced into the reaction medium concurrently with the other reactants but it is preferred to react the borane with an alkali metal cyanide, e.g., sodium cyanide before contacting the boron compound with the above-described metal salt. The resultant alkali metal adduct is more stable than the free borane and is readily dissolved in the reaction medium. Illustrative of boranes which are operable in the present invention are triphenyl borane, triorthotolyl borane, triparatolylborane, triparachlorophenylborane, trixylylborane, tris-(3,4,5-trimethylphenyl)borane and trinaphthylborane.

The nitriles (corresponding to the ligands $R_{1-4}CN$ in the above formula) which are contacted with the other reactants include monofunctional nitriles, e.g., 2-methyl-2-butenenitrile, 2-methyl-3-butenenitrile 2-pentenenitrile, 3-pentenenitrile, 4-pentenenitrile, valeronitrile, butyronitrile, isobutyronitrile, propionitrile, acetonitrile, pentanonitrile, hexanonitrile, acrylonitrile, 2-butenenitrile, 2-hexenenitrile and 2-heptenenitrile, and difunctional nitriles, e.g., adiponitrile, methyl glutaronitrile, ethyl succinonitrile, methylene glutaronitrile, pimelonitrile, suberonitrile, azelonitrile and sebaconitrile.

The reaction can be conducted in the presence or absence of added solvent since the nitriles can act as a solvent or reaction medium. Generally common organic solvents such as methylene chloride, chloroform, toluene, and chlorobenzene, which are inert to the reactants and product can be employed if a solvent is desired. Other solvents should be apparent to one skilled in the art.

The reaction can be conducted over a wide range of temperature usually 0° to 100° C. and preferably 20° to 55° C. Agitation can be provided, if desired.

It is preferred to prereact the cyanide with the triarylborane before the introduction of the other reactants although all the reactants can be added simultaneously. The metal salt should not be permitted to remain in contact with the source of cyanide for any appreciable time in the absence of the other reactants since these two compounds can react to form a metal cyanide and thereby decrease the yield of the desired complex.

In some instances, because of the solubility or availability of some of the reagents, it may be desirable to first prepare a soluble mononitrile complex, e.g., the complex formed from 3-pentenenitrile, the metal salt, an alkali metal cyanide and a triarylborane by the means discussed above. These complexes will generally be found to be soluble in the reaction medium. Should an insoluble dinitrile complex be desired, the addition of the dinitrile to the soluble complex will cause the precipitation of the dinitrile complex, except, of course, in such cases where the dinitrile complex is soluble itself.

In other instances, particularly in cases where small quantitites of valuable reagents must be used, it is often desirable to synthesize an aquated complex, e.g., the complex formed from nickel chloride hexahydrate and sodium cyanotriphenylborate in aqueous solution, and then slurry this complex in a warm nitrile solvent that forms a low-boiling azeotrope with water. The water will be carried over and the new complex, e.g., $Ni[NCCH_3]_4[NC^{13}BO_3]_2$, may be isolated by standard techniques.

The following Examples are presented to illustrate but not to restrict the present invention. Parts and percentages are by weight unless otherwise specified.

EXAMPLE 1

Approximately 40 parts of sodium cyanotriphenylborate, 16.33 parts of nickel (II) chloride hexahydrate and 500 parts of adiponitrile were combined and agitated at 20° C. for 48 hours. The solids which formed during agitation were removed by filtration, washed with toluene and then dried in a vacuum oven. The dry solids were mixed well with 750 parts of acetone and then with 40 parts of water. The mixture was heated nearly to boiling (by which time most of the solids had dissolved), filtered, and cooled to 20° C. About 3,000 parts of water were added to the cooled solution whereupon a precipitate formed. The mixture was stirred for an additional hour at room temperature and then filtered. The precipitate was washed with water and dried in a vacuum oven at 45° C. The recovered solids gave the characteristic infrared bands at 2220 cm$^{-1}$ and 2300 cm$^{-1}$. An elemental analysis gave the following results:

| Element | C | H | N | B | Ni |
|---------|------|------|-------|------|------|
| Expected | 74.03% | 5.72% | 10.36% | 2.66% | 7.24% |
| Found | 73.48% | 6.00% | 9.90% | 2.47% | 7.14% |

EXAMPLE 2

Approximately 100 parts of adiponitrile, 3.4 parts of sodium cyanide and 100 parts of a 16.92% solution of triphenylborane in 3-pentenenitrile were stirred together at 20° C. for 15 min. while sparging the liquid with nitrogen. Following which 11.5 parts of magnesium chloride hexahydrate were added. After one hour at 20° C. a precipitate had formed which was removed by filtration. Two volumes of adiponitrile were added to the filtrate at 20° C., which resulted in a snow-white precipitate. This precipitate was recovered and dried under vacuum at 60° C. It gave the characteristic bands at 2195 cm$^{-1}$ and 2285 cm$^{-1}$. An elemental analysis gave the following results:

| Element  | C      | H     | N      | B     | Mg    |
|----------|--------|-------|--------|-------|-------|
| Expected | 77.30% | 5.97% | 10.82% | 2.78% | 3.13% |
| Found    | 78.40% | 6.20% | 10.74% | 3.18% | 2.74% |

EXAMPLE 3

Mn[NC(CH$_2$)$_4$CN]$_2$[NCBO$_3$]$_2$

Approximately 51 parts of an 18% solution of triphenylborane in 3-pentenenitrile, 13 parts of 3-pentenenitrile, and 2.0 parts of sodium cyanide were stirred together at 50° C. for 30 minutes, at which time all the sodium cyanide dissolved. Manganese (II) nitrate hexahydrate (7.5 parts) was added to the solution which was held at 50° C. for three hours. All solids which formed were filtered off to give a clear solution. Approximately 20 parts of adiponitrile were added to 20 parts of the solution thus obtained. A white precipitate which formed overnight was filtered off, washed with toluene, then cyclohexane and dried. It gave the characteristic infrared pattern at 2195 cm$^{-1}$ and 2275 cm$^{-1}$.

EXAMPLE 4

Fe[NC(CH$_2$)$_4$CN]$_2$[NCBO$_3$]$_2$

Approximately 1.0 part of ferrous sulfate heptahydrate, 2.09 parts of sodium cyanotriphenylborate and 40 parts of adiponitrile were combined and stirred under a nitrogen atmosphere at 20° C. for 20 hours. The precipitate which formed during the stirring was recovered by filtration, washed first with toluene, and then hexane and, finally, dried. Infrared analysis indicated characteristic bands at 2195 cm$^{-1}$ and 2275 cm$^{-1}$. An elemental analysis gave the following results:

| Element  | C      | H     | N      | B     | Fe    |
|----------|--------|-------|--------|-------|-------|
| Expected | 74.28% | 5.74% | 10.40% | 2.68% | 6.91% |
| Found    | 74.16% | 5.86% | 10.41% | 2.78% | 6.66% |

EXAMPLE 5

Co[NC(CH$_2$)$_4$CN]$_2$[NCBO$_3$]$_2$

Cobaltous chloride hexahydrate (0.817 part), 2.0 parts of sodium cyanotriphenylborate and 40 parts of adiponitrile were combined and stirred at 20° C. for approximately 17½ hours. The precipitate which formed during the stirring was recovered by filtration, washed with toluene then hexane and dried. The product exhibited characteristic infrared bands at 2205 cm$^{-1}$ and 2285 cm$^{-1}$.

EXAMPLE 6

Zn[NC(CH$_2$)$_4$CN]$_2$[NCBO$_3$]$_2$

Approximately 5.0 parts of sodium cyanotriphenylborate, 2.55 parts of zinc (II) nitrate and 100 pats of adiponitrile were combined and stirred together at 20° C. for about 72 hours during which time a precipitate formed. The precipitate was recovered by filtration, washed with toluene and then water. It was dissolved in acetone. The acetone solution was then evaporated to dryness and the solid, analyzed by infrared spectrophotometry, showed the characteristic bands at 2220 cm$^{-1}$ and 2290 cm$^{-1}$. Atomic absorption analysis indicated 7.59% Zn (calculated 7.99%) and 2.37% B (calculated 2.64%).

EXAMPLE 7

Cd[NC(CH$_2$)$_4$CN]$_2$[NCBO$_3$]$_2$

Approximately 5.0 parts of sodium cyanotriphenylborate, 2.23 parts of cadmium (II) chloride hydrate and 50 parts of adiponitrile were combined and stirred for 20 hours at 20° C. during which time a precipitate formed. The precipitate was recovered by filtration, washed twice with approximately 2 volumes of toluene and dried. The dried precipitate was combined with 75 parts of acetone and 4 parts of water. The resultant slurry was heated to 50° C. and then filtered. The filtrate was then cooled to 20° C. and poured into 300 parts of water at 20° C. After approximately one hour a precipitate formed and was recovered by filtration, washed twice with water and dried. Infrared spectrophotometric analysis showed the characteristic isonitrile band at 2195 cm$^{-1}$, an unbound alkylnitrile band at 2250 cm$^{-1}$ and a bound one at 2270 cm$^{-1}$. An elemental analysis of the compound showed the following:

| Element  | C      | H     | N     | B     | Cd     |
|----------|--------|-------|-------|-------|--------|
| Expected | 69.43% | 5.36% | 9.72% | 2.50% | 12.99% |
| Found    | 68.16% | 5.50% | 9.18% | 2.41% | 13.88% |

EXAMPLE 8

Mn[NCCH(CH$_3$)(CH$_2$)$_2$CN]$_2$[NCBO$_3$]$_2$

To approximately 51 parts of the solution obtained in Example 3 prior to the final addition of adiponitrile were added 21.3 parts of methyl glutaronitrile and the mixture was permitted to stand for 24 hours following which 19 parts of methyl glutaronitrile were added. The resultant mixture was heated to 50° C. with stirring for 30 minutes then cooled to 20° C. and extracted with two 300 part washes of cyclohexane at 20° C. The remaining solution was then mixed with 300 parts of toluene and allowed to stand for one hour at room temperature then heated to 50° C. with stirring for three hours during which time a white precipitate formed. The precipitate was recovered by filtration, washed first with toluene and then with cyclohexane and, finally, dried. The infrared spectrophotometric analysis showed the characteristic bands at 2210 cm$^{-1}$ and 2290 cm$^{-1}$.

EXAMPLE 9

Fe[NCCH(CH$_3$)(CH$_2$)$_2$CN]$_2$[NCBO$_3$]$_2$

Approximately 7.16 parts of ferrous sulfate heptahydrate, 15 grams of sodium cyanotriphenylborate and 100 parts of methyl glutaronitrile were stirred together at room temperature for 14 days during which time a precipitate formed. The precipitate was recovered by filtration, washed twice with approximately 20 parts of toluene and dried in a vacuum oven. About 5.0 parts of the dried precipitate were added to 75 parts of acetone and 4 parts of water following which the mixture was heated to approximately 50° C. filtered through filter paper, and added to 300 parts of water, while stirring. The resultant mixture was permitted to stand at room temperature for 30 minutes during which time a precipitate was formed. The precipitate was removed by filtration, washed twice with approximately 20 parts of water and dried. Infrared spectrophotometric analysis showed characteristic peaks at 2190 cm$^{-1}$ and 2265 cm$^{-1}$. An elemental analysis indicated the following:

| Element | C | H | N | B | Fe |
|---|---|---|---|---|---|
| Expected | 74.29% | 5.74% | 10.40% | 2.67% | 6.91% |
| Found | 74.26% | 6.06% | 9.97% | 2.52% | 6.58% |

EXAMPLE 10

Ni[NCCH$_3$]$_4$[NC$^{13}$BO$_3$]$_2$

Approximately 1.24 parts of triphenylborane were dissolved in 40 parts of acetonitrile under a nitrogen atmosphere. To this solution, still maintained under a nitrogen atmosphere, was added with stirring 0.26 part of carbon-13 labelled sodium cyanide dissolved in 10 part of water and then 10 parts of sodium chloride. The mixture was stirred for 30 minutes then removed from the nitrogen atmosphere, filtered and placed in a separatory funnel. The lower brine layer was discarded. The upper layer was passed through dry filter paper and then evaporated to dryness under vacuum. A slightly gummy residue of NaNC$^{13}$BO$_3$ was obtained.

Approximately 1.25 parts of NaNC$^{13}$BO$_3$, prepared as above, were dissolved in 20 parts water. This solution was then added to approximately 0.5 part of nickel chloride hexahydrate dissolved in 20 parts of water. After 30 minutes a precipitate formed. The precipitate was filtered off, then reslurried in 20 parts water and refiltered. After being reslurried and refiltered once more, the solid was dried on a filter under a nitrogen stream at 20° C. The dried solid was then added to 100 parts of acetonitrile. The mixture was heated to 75° C. and then cooled to 20° C. while being sparged with nitrogen. Approximately 500 parts of carbon tetrachloride were then added. After two hours a flocculent precipitate which had formed was removed by filtration and the filtrate evaporated to dryness under vacuum while maintaining the temperature at less than 35° C. The resultant solid showed the forked infrared nitrile resonance of acetonitrile at 2280 and 2300 cm$^{-1}$ and the cyanoborate resonance at 2150 cm$^{-1}$.

EXAMPLE 11

Ni[NCC(:CH$_2$)(CH$_2$)$_2$CN]$_2$[NCBO$_3$]$_2$

Approximately 2.0 parts of sodium cyanotriphenylborate and 1.63 parts of nickel (II) chloride hexahydrate were stirred in 25 ml of methylene glutaronitrile for 47 hours. A precipitate formed which was isolated by filtration, washed with toluene and dried. Infrared spectrophotometric analysis showed an isonitrile band at 2215 cm$^{-1}$, plus two nitriles at 2265 cm$^{-1}$ and 2295 cm$^{-1}$. These are expected as uncomplexed methylene glutaronitrile itself has nonequivalent nitriles at 2220 cm$^{-1}$ and 2250 cm$^{-1}$.

EXAMPLE 12

Cu[NC(CH$_2$)$_4$CN]$_2$[NCBO$_3$]$_2$

Approximately 2.0 parts of sodium cyanotriphenylborate and 0.586 part of copper (II) chloride dihydrate were stirred in 40 parts of adiponitrile for 17½ hours at room temperature. The precipitate which formed was recovered by filtration, washed three times with toluene, then washed once with hexane and dried. Infrared spectrophotometric analysis of the solid showed the characteristic bands for the metal coordinated cyanotriphenylborate and alkylnitrile.

I claim:

1. Compounds having the general formula:

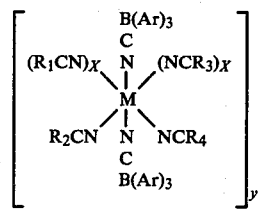

wherein X is 0 or 1, Y is a positive integer of 1–50, M is a metal selected from the group of metals of groups IIA, IB, IIB, VIIB and VIII; provided that when M is Pd, Ag, Cd, Pt, Au or Hg, X is 0; Ar is an aryl or substituted aryl group having 6–10 carbon atoms; R$_1$, R$_2$, R$_3$ and R$_4$ are the same or different and are selected from groups consisting of alkyl and substituted alkyl groups having 1–6 carbon atoms, alkenyl and substituted alkenyl groups having 2–6 carbon atoms, aryl groups having 6–10 carbon atoms and when adjacent nitrile groups are cojoined alkylene groups having 1–4 carbon atoms.

2. The compound of claim 1 where M is selected from the group consisting of Mg, Mn, Fe, Co, Ni, Cu and Zn and X is 1 and Cd and X is 0.

3. The compound of claim 1 wherein Ar is a group selected from the group consisting of phenyl and tolyl.

4. The compound of claim 1 wherein M is a metal selected from the group consisting of divalent nickel, divalent iron and trivalent iron and X is 1.

5. The compound of claim 1 wherein the adjacent nitrile groups are cojoined with ethylene groups.

6. The compound of claim 2 wherein the adjacent nitrile groups are cojoined with ethylene groups.

7. The compound of claims 3 or 4 wherein the nitrile groups are cojoined with ethylene groups.

8. The compound of claim 5 wherein M is divalent nickel and Ar is phenyl.

9. A compound of the formula [Ni[NC(CH$_2$)$_4$CN]$_2$[NCBO$_3$]$_2$]$_y$ wherein y is a positive integer of from 1 to about 20.

10. Compounds of the general formula:

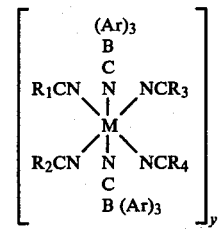

wherein Y is a positive integer of of 1–50; M is metal selected from the group consisting of Ni$^{++}$, Fe$^{++}$ and Fe$^{+++}$; Ar is selected from the group consisting of phenyl, orthotolyl, paratolyl and mixtures thereof; R$^1$–R$_4$ are the same or different and are selected from groups consisting of 1-methyl-1-propenyl, 1-methyl-2-propenyl, 1-butenyl, 2-butenyl, 3-butenyl, butyl, and when adjacent nitrile groups are cojoined ethylidene and ethylene.

* * * * *

UNITED STATES PATENT OFFICE
CERTIFICATE OF CORRECTION

PATENT NO. : 4,394,321

DATED : July 19, 1983

INVENTOR(S) : MICHAEL M. CONE

It is certified that error appears in the above-identified patent and that said Letters Patent are hereby corrected as shown below:

The title should read -- TRIARYLBORANEISOCYANO METAL COMPOUNDS --.

Column 1, line 18, "$O_3$" should be -- $\phi_3$ --.

Column 1, line 20, "$BO_3$" should be -- $B\phi_3$ --.

Column 1, line 21, "$BO_3$" should be -- $B\phi_3$ --.

Column 1, line 24, "$BO_3$" should be -- $B\phi_3$ --.

Column 4, line 17, "$BO_3$" should be -- $B\phi_3$ --.

Column 4, line 26, "$BO_3$" should be -- $B\phi_3$ --.

Column 4, line 54, "$BO_3$" should be -- $B\phi_3$ --.

Column 5, line 10, "$BO_3$" should be -- $B\phi_3$ --.

Column 5, line 26, "$BO_3$" should be -- $B\phi_3$ --.

Column 5, line 45, "$BO_3$" should be -- $B\phi_3$ --.

Column 5, line 57, "$BO_3$" should be -- $B\phi_3$ --.

Column 6, line 5, "$BO_3$" should be -- $B\phi_3$ --.

Column 6, line 31, "$BO_3$" should be -- $B\phi_3$ --.

Column 6, line 51, "$BO_3$" should be -- $B\phi_3$ --.

Column 7, line 11, "$BO_3$" should be -- $B\phi_3$ --.

UNITED STATES PATENT OFFICE
CERTIFICATE OF CORRECTION

PATENT NO. : 4,394,321  
DATED : July 19, 1983  
INVENTOR(S) : MICHAEL M. CONE

Page 2 of 2

It is certified that error appears in the above-identified patent and that said Letters Patent are hereby corrected as shown below:

Column 7, line 24, "$BO_3$" should be -- $BØ_3$ --.

Column 7, line 25, "$BO_3$" should be -- $BØ_3$ --.

Column 7, line 46, "$BO_3$" should be -- $BØ_3$ --.

Column 7, line 60, "$BO_3$" should be -- $BØ_3$ --.

Claim 9, Column 8, line 44, "$BO_3$" should be -- $BO_3$ --.

Claim 10, Column 8, line 58, the first "of" should be deleted.

Signed and Sealed this

Eighth Day of May 1984

[SEAL]

Attest:

Attesting Officer

GERALD J. MOSSINGHOFF

Commissioner of Patents and Trademarks